United States Patent [19]

Fazan et al.

[11] Patent Number: 5,503,842
[45] Date of Patent: Apr. 2, 1996

[54] POLYTETRAFLUOROETHYLENE THERAPEUTIC ARTICLES

[75] Inventors: Stephen A. Fazan, Flemington; Bernie L. Blackwell, Hackensack; John P. Curtis, Bloomsbury; James H. Kemp, Piscataway, all of N.J.

[73] Assignee: Colgate-Palmolive Company, New York, N.Y.

[21] Appl. No.: 260,621

[22] Filed: Jun. 16, 1994

Related U.S. Application Data

[63] Continuation of Ser. No. 454,632, Oct. 16, 1989, abandoned.

[51] Int. Cl.$^6$ ............................................. A61F 13/00
[52] U.S. Cl. ............................................. 424/443; 424/400
[58] Field of Search ............................ 424/443, 442, 424/435, 70

[56] References Cited

U.S. PATENT DOCUMENTS

| | | | |
|---|---|---|---|
| 3,830,246 | 8/1974 | Gillings | 132/89 |
| 4,462,136 | 7/1984 | Nakao | 132/321 |
| 4,548,219 | 10/1985 | Newman | 424/70 |
| 4,554,154 | 11/1985 | White | 424/443 |
| 4,583,564 | 4/1986 | Finkelstein | 132/321 |
| 4,594,242 | 6/1986 | Naganuma | 433/216 |
| 4,610,872 | 9/1986 | Lynch | 424/49 |
| 4,776,358 | 10/1988 | Lorch | 433/216 |
| 4,836,226 | 6/1989 | Wolak | 132/321 |
| 4,892,736 | 1/1990 | Goodson | 424/443 |
| 4,911,927 | 3/1990 | Hill | 424/443 |
| 4,921,692 | 5/1990 | Gaffar | 424/52 |
| 4,923,684 | 5/1990 | Ibrahim | 424/52 |

FOREIGN PATENT DOCUMENTS

| | | |
|---|---|---|
| 0335466 | 10/1989 | European Pat. Off. . |
| 946643 | 1/1964 | United Kingdom . |

*Primary Examiner*—Thurman K. Page
*Assistant Examiner*—William E. Benston, Jr.
*Attorney, Agent, or Firm*—M. J. McGreal; R. C. Sullivan

[57] ABSTRACT

Polytetrafluoroethylene surfaced articles can be coated with various adjuvants such as medicants and flavorants. The coated articles can be dental flosses, toothpicks, and tongue depressors. The dental flosses can be of a monofilament or a multi-filament type. Further, they can be a filament of polytetrafluoroethylene or have a coating of polytetrafluoroethylene.

26 Claims, No Drawings

POLYTETRAFLUOROETHYLENE THERAPEUTIC ARTICLES

This application is a continuation of U.S. application Ser. No. 07/454,632 filed Oct. 16, 1989, now abandoned.

BACKGROUND OF THE INVENTION

The present invention is directed to polytetrafluoroethylene surfaced articles which contain thereon an adjuvant material. More particularly, the present invention is directed to polytetrafluoroethylene therapeutic articles for use in the oral cavity and which have thereon an adjuvant substance such as a medicant and/or flavorant.

Polytetrafluoroethylene is a material which is well known for its surface lubricity. Polytetrafluoroethylene due to its compact carbon and fluorine structure has the property whereby the surface is highly resistant to the adhesion of most substances. In fact, it is this property of polytetrafluoroethylene that has been primarily utilized in the design of various articles. When it is desired to have a surface to which other substances will not adhere, it is common to coat that surface with a layer of polytetrafluoroethylene. The use of polytetrafluoroethylene is enhanced since it can withstand high temperatures. This is the case with regard to platens, pans, rollers, and the like. The lower degree of adhesion of polytetrafluoroethylene for most substances provides an effective technique for processing materials through machinery and not having such materials adhere to parts of the machinery and to otherwise create problems in the operation of such machinery. However, just as polytetrafluoroethylene has many effective uses where it is desired that other materials not adhere to its surface, it is difficult to intentionally adhere substances to its surface.

In the design and construction of various articles for therapeutic use in the oral cavity, it is desirable to use polytetrafluoroethylene articles or polytetrafluoroethylene coated articles for this purpose. Polytetrafluoroethylene has many properties which are useful in the design and construction of the therapeutic articles. However, it is likewise desirable in many instances for such articles to have a coating of a medicant and/or a flavorant. This presents the difficulty of how to get a medicant and/or a flavorant effectively adhered to the surface of polytetrafluoroethylene. This problem is made all the more difficult when it is considered that the articles after being coated with the medicant and/or flavorant must be able to undergo subsequent processing, packaging, handling and usage without the medicant or flavorant unintentionally becoming detached from the polytetrafluoroethylene surface.

One very useful therapeutic article that can be constructed from polytetrafluoroethylene is dental floss. This can be a monofilament or a multi-filament dental floss. It has been found that a monofilament of polytetrafluoroethylene is a very effective dental floss. This can be a monofilament of polytetrafluoroethylene or a nylon, dacron, or other filament coated with polytetrafluoroethylene. A polytetrafluoroethylene monofilament dental floss or a polytetrafluoroethylene surfaced monofilament dental floss will have a thickness to width ratio of at least about 1 to 10, and preferably about 1 to 50 to about 1 to 500. The width of the monofilament will be at least 10 times the thickness, and preferably about 50 to 500 times the thickness of the polytetrafluoroethylene monofilament. A polytetrafluoroethylene dental floss having such a thickness to width ratio can be easily inserted between teeth for the removal of substances adhering to the teeth as well as for removing food particles from between the teeth. When in the form of a multi-filament floss, each strand will be of a diameter of about 0.1 to 0.001 millimeters and will consist of from about 10 to 1000 fibers. These fibers will be in a twisted arrangement. A problem is that it has not been possible to provide either a medicant or a flavorant coating on such a dental floss product. This is the case, since as discussed above, the surface of polytetrafluoroethylene has a high lubricity to which substances adhere only with difficulty.

Most of the dental floss products that are available today are multi-filament materials. These multi-filament materials include nylons such as nylon 6 and nylon 66, rayons, dacron, acetate polymers, polypropylene polymers, cotton, wool and other natural fibers. Examples of such multi-filament dental flosses are set forth in U.S. Pat. Nos. 3,897,795, 3,943,949, 4,033,365, 4,414,990, 4,548,219, 4,583,564 and 4,638,823. These fibers that are usually used in producing multi-filament dental flosses have surfaces to which it is rather easy to adhere various medicants and/or flavorants. Further, the very nature of the multi-filament structure of such flosses also makes it easier to adhere a medicant and/or a flavorant. That is, the medicant and/or flavorant can be held within the interstices between the individual fibers which make up the multi-filament dental floss. The foregoing patents which have been cited to illustrate multi-filament dental flosses also disclose having various adjuvants as a part of the dental floss and techniques for adhering these various adjuvants to the multi-filament dental flosses.

Monofilament dental flosses are known. In U.S. Pat. Nos. 3,800,812 and 4,617,950, there are disclosed monofilament dental floss products. In U.S. Pat. No. 3,800,812, the dental floss is disclosed to be an elastomeric monofilament material. In U.S. Pat. No. 4,617,950, the fibers that are disclosed to be useful as a monofilament comprise the fibers that are conventionally used to make dental flosses. However, neither of these patents discloses a dental floss which is comprised of an effectively coated polytetrafluoroethylene monofilament. In U.S. Pat. No. 4,776,358 there is disclosed a polytetrafluoroethylene dental floss. However, this dental floss is not a coated monofilament floss. In addition, the dental floss that is disclosed in this patent contains a paste which is sandwiched between two pieces of polytetrafluoroethylene. The objective in this patent is to have the dentifrice that is contained within the floss flow from the floss while the floss is being used. There is no disclosure in this patent with regard to adhering a medicant, flavorant or other substance to the surface of polytetrafluoroethylene. There is also available a monofilament, polytetrafluoroethylene dental floss. However, this floss is not coated with any medicants, flavorants or related substances.

The problem of adhering a medicant, flavorant or related substance to the surface of polytetrafluoroethylene has now been solved. A composition has been found which will adhere to the surface of polytetrafluoroethylene and which will not be removed during any further processing, packaging or handling. That is, a medicant and/or flavorant will be substantially maintained on the polytetrafluoroethylene surface until the point in time that it is to be removed from the polytetrafluoroethylene surface. It is therefore now possible to provide polytetrafluoroethylene articles, or polytetrafluoroethylene surfaced articles, which have a coating of a medicant and/or a flavorant. Such articles, as previously noted, are effective for therapeutic purposes. In particular, such articles such as dental floss, tooth picks, dental tape, tongue depressors and the like can be more effectively used.

BRIEF DESCRIPTION OF THE INVENTION

The present invention is directed to polytetrafluoroethylene or polytetrafluoroethylene surfaced articles which have a coating adhered thereon. More particularly, the present invention is directed to therapeutic articles which have a coating of a medicant, and/or a flavorant and which can be utilized in the oral cavity. It has been found that as a part of a certain composition, a medicant and/or a flavorant can be adhered to the surface of polytetrafluoroethylene. This adhesion to the surface of polytetrafluoroethylene is sufficiently strong so that it is not removed frown the polytetrafluoroethylene surface during further processing, packaging or handling. However, during usage as a floss, the medicant and/or flavorant will be dissolved from the surface of the floss. A medicant and/or flavorant is applied to the surface of polytetrafluoroethylene from an aqueous emulsion which contains the medicants and/or flavorants ad other adjuvants and which, in addition, contains polyvinyl alcohol and polyethylene glycol. If the composition is to be a flavorant, it may also contain a sweetener, and preferably a non-carbohydrate sweetener. This composition is applied to the polytetrafluoroethylene surface from an aqueous emulsion. After the aqueous emulsion is applied to the surface of the polytetrafluoroethylene, the polytetrafluoroethylene is dried with the medicant and/or flavorant thereby adhering to the polytetrafluoroethylene surface.

DETAILED DESCRIPTION OF THE INVENTION

As has been noted above, it is difficult to adhere substances to the surface of polytetrafluoroethylene. This is the case regardless of the type of polytetrafluoroethylene. This can be an expanded or non-expanded polytetrafluoroethylene. It can also be a monofilament or a multi-filament polytetrafluoroethylene. Further, this is the case whether an article is constructed entirely of polytetrafluoroethylene or if it only contains a polytetrafluoroethylene surface. Due to the high surface lubricity of polytetrafluoroethylene, it is difficult to get substances to adhere to its surface. This applies to medicants and/or flavorants which include fluorides, antiplaque, anti-caries, anti-bacterial and tartar control agents, coagulants, coolants, colorants and polishing agents. However, it has been found useful to have medicants and/or flavorants as a part of the surface of various therapeutic articles that are to be used in the oral cavity. That is, it has been found to be useful and desirable to have medicants and/or flavorants on the surface of therapeutic articles such as tooth picks, tongue depressors and dental floss. It has also been found to be useful to have such therapeutic articles constructed of polytetrafluoroethylene, or to have a polytetrafluoroethylene surface. This is particularly the case with regard to dental floss. This can be a multi-filament dental floss, but it has been found to be very effective to utilize a monofilament of polytetrafluoroethylene as a dental floss. This dental floss is highly resistant to breaking, has an inherent lubricity which makes it easier to insert between teeth, and due to its shape is very effective in removing substances from teeth as well as for removing food particles from between teeth.

A useful polytetrafluoroethylene for a dental floss is an expanded polytetrafluoroethylene in a tape form. Such a polytetrafluoroethylene has a tensile strength of at least about 8000 pound per square inch (psi) (68,950 pPa) and a polymeric matrix strength in excess of about 100,000 psi (689,500 kPa). Such a polytetrafluoroethylene also has a porosity of at least about 90 percent. However, a conventional extruded and calendered tape form of polytetrafluoroethylene can also be used. In addition, an essentially circular cross-section polytetrafluoroethylene filament can be used.

Medicants, flavorants and other substances can be adhered to the surface of polytetrafluoroethylene through the use of a polymer which has an affinity for the surface of polytetrafluoroethylene and which is at least partially water soluble. The binder must be at least partially water soluble so that an effective amount of the medicant and/or flavorant can be released. Although any compositions which have a high degree of adherence to polytetrafluoroethylene and which are at least partially water soluble, can be used, a preferred composition consists of polyvinyl alcohol and polyethylene glycol as the adhering agents. It has been found that an aqueous emulsion containing polyvinyl alcohol and polyethylene glycol can be effectively utilized to adhere medicants and/or flavorants to the surface of polytetrafluoroethylene. In one embodiment, the medicants and/or flavorants are made a part of the aqueous emulsion of polyvinyl alcohol and polyethylene glycol. In such an instance, the medicants and/or flavorants must be at least partially soluble in the aqueous emulsion medium. In order to coat the polytetrafluoroethylene surfaced articles, it is only necessary to contact the article with the emulsion. After contact with the emulsion, the article is then dried to remove moisture and to thereby set the polyvinyl alcohol-polyethylene glycol composition onto the polytetrafluoroethylene surface. This dried polyvinyl alcohol-polyethylene glycol composition will also contain the medicants and/or flavorants which were a part of the coating emulsion. If the medicants and/or flavorants are not significantly soluble in the emulsion composition, other solvents can be added in order to increase the solubility of the medicants and/or flavorants in the emulsion composition. The most effective way to apply the medicants and/or flavorants to a polytetrafluoroethylene surface is by having the medicants and/or flavorants dissolved in the emulsion composition.

The medicants that can be added include the K vitamins (1–4), calcium ions and blood factors which initiate the blood cascade. In addition, the medicant can include coagulants such as aminocaproic acid, tranexamic acid, adrenaline, alum, noradrenaline, iron salts, zinc salts and calcium alguate. Other coagulants and other medicants can also be used. Other medicants include antibiotics such as tetracycline, cetyl pyridinium chloride, benzethonium chloride and other quaternary salts, chlorhexidine, hexachlorophene and wound healing agents such as allantoin and zinc sulfate. In addition, the composition can contain a preservative such as sodium benzoate, citric acid, benzoic acid, ascorbic acid and erythrobic acid.

The composition may also contain a dentally accept colorant such as FD&C red 3 and FD&C red 4.

The fluoride agents that can be a part of the composition include sodium fluoride, sodium monofluoride phosphate and stannous fluoride. A dentally accepted cooling agent such as menthol or analogues such as N-ether-p-methane-3-carboxamide can also be a part of the composition. In addition, there can be present a polishing agent such as a water insoluble phosphate, amorphous silica, alumina or calcium carbonate.

The anticalculus agents include the linear molecularly dehydrated alkali metal or ammonium salts of such as sodium hexametaphosphate, sodium tripolyphosphate, dissodium diacid phosphate, trisodium monoacid phosphate, tetrasodium polyphosphate and polyphosphates having the general formula of $(NaPO_3)_n$ where n is 2 to 125. This polyphosphate and other phosphates are preferably used in conjunction with synthetic anionic linear polymeric polycarboxylates. These include copolymers of maleic anhydride or acid with methyl vinyl ether having a molecular weight of 30,000 to 1,000,000 and available under the tradenames Gantrez AN 139, Gantrez AN 119 and Gantrez S-97.

A sweetener can also be a part of the composition. Preferably, such a sweetener is a non-carbohydrate sweetener such as sodium saccharin or phenylalanine.

The preferred emulsion composition will contain from about 40 to 80% by weight water, about 5 to 20% by weight polyvinyl alcohol, about 10 to 40% by weight of the medicants, flavorants, and other additives, and about 1 to 4% by weight of polyethylene glycol. Most preferably, the emulsion composition will contain about 67% by weight water, about 10% by weight polyvinyl alcohol, about 20% by weight of medicants, flavorants and other additives, and about 2% by weight of polyethylene glycol.

The various adjuvants, amounts of the various adjuvants, that will be a part of a composition will depend on the particular adjuvant and the composition. An artificial sweetener will range in content from about 0.25 to 1.0 percent by weight. A flavorant will be present in an amount of about 5 to 25 percent by weight depending on the flavorant. When present, an anti-calculus agent will be present in an amount of about 0.5 to 10 percent by weight. The fluoride agent will be present in an amount of about 0.005 to 1 percent by weight. A polishing agent, if present, will be in a content of up to about 4 percent by weight. Each of antibiotics, coagulants, wound healing agents, preservatives, coolants and colorants will be present in an amount of up to about 2 percent by weight.

The polytetrafluoroethylene therapeutic articles that can most usefully be coated with medicants and/or flavorants are dental flosses. In one embodiment, the dental floss is a monofilament strand of polytetrafluoroethylene, or a polytetrafluoroethylene coating on a base fiber. The base fiber can be nylon, dacron, acetate polymers, polypropylene, cotton, wool or other fiber. This monofilament strand has a thickness of about 0.001–0.003 mm and a thickness to width and a ratio of at least 1 to 10, and preferably a thickness to width ratio of between about 1:50 to about 1:500. That is, the dental floss is considerably wider than it is thick. In preparing this dental floss, the monofilament strand of polytetrafluoroethylene is fed through a bath of the above aqueous emulsion composition which contains the polyvinyl alcohol, polyethylene glycol, medicants and/or flavorants. As the strand of polytetrafluoroethylene passes through the bath, it picks up a sufficient amount of the emulsion composition and is then passed into a drying chamber. This drying chamber can be a tube surrounded by heating elements and having an inlet for the flow of air. Air that is flowed into the drying chamber will purge the drying chamber of moisture. The strand of polytetrafluoroethylene leaves the drying chamber with the non-water components of the emulsion coating composition adhered to the polytetrafluoroethylene surface. This now coated strand of polytetrafluoroethylene is wound on a spool and can be utilized for dental flossing.

In addition to the dental floss being a monofilament polytetrafluoroethylene, or a base fiber coated with polytetrafluoroethylene, it can also be a multi-filament dental floss. Each component filament can be a polytetrafluoroethylene filament or a base fiber coated with polytetrafluoroethylene. The base fiber can be essentially any fiber such as those set out above. Each filament that makes up the multi-filament strand of dental floss will be of a diameter of about 0.1 to 0.001 millimeters and will consist of from about 10 to 1000 fibers. These fibers will be in a twisted arrangement. The coating on the polytetrafluoroethylene surface which serves to bond the medicants and/or flavorants to the fiber also will decrease the lubricity of the polytetrafluoroethylene surface to such a point that the fibers will maintain a twisted arrangement until used. When used, such a multi-filament dental floss will become splayed into a more flat shape. This will be a shape similar to that of the monofilament dental floss.

Each filament of the multi-filament dental floss preferably will be coated with the medicant and/or flavorant using the method for coating the polytetrafluoroethylene monofilament dental floss. Likewise, any of the compositions used for coating the polytetrafluoroethylene monofilament can be use for coating the strands of the multi-filament floss. After coating the strands would then be formed into the multi-filament floss. However, it is also feasible to first form the multi-filament floss and then to apply the coating. The processing steps of applying the coating would be essentially the same.

A particular advantage to the present coatings on a strand of polytetrafluoroethylene is that it serves to reduce the lubricity of the surface of the polytetrafluoroethylene whereby the polytetrafluoroethylene strand can more easily be wound and otherwise manipulated. An uncoated polytetrafluoroethylene strand due to its high lubricity presents difficulties in winding due to slippage of the fibers, one over another. This is an unexpected advantage with regard to these coatings.

When it is desired to use these coated polytetrafluoroethylene as a dental floss, a segment of the polytetrafluoroethylene floss, whether a monofilament or a multi-filament, is removed from the spool and is used in the manner of other dental flosses. During flossing, the medicants and/or flavorants that had been coated onto the surface of the polytetrafluoroethylene are released and utilized in the oral cavity. These medicants and/or flavorants are released since the dried coating when in contact with saliva in a persons mouth will become redissolved and reemulsified and thereby stripped from the surface of the polytetrafluoroethylene.

The present invention will now be set forth in more detail with reference to the following examples.

Examples 1–5

These examples illustrate the coating of an expanded microporous polytetrafluoroethylene tape having a thickness of 0.001–0.002 mm and width of 2–3 mm with fluoride and an anti-calculus agent medicants. This tape is unwound from a spool and passed through a coating both which contains the coating solution. The polytetrafluoroethylene tape containing the wet coating is then passed through a drier maintained at above 100° C. The polytetrafluoroethylene tape is in a last step, wound onto a spool. The composition of the coating solution in grams for each of the examples is set out in Table 1.

TABLE 2

| Example | Polyvinyl Alcohol | Polyethylene Glycol 4000 | Sodium Fluoride | Glycerine | Gantrez S-97 | Tetrasodium Polyphosphate | Water |
|---|---|---|---|---|---|---|---|
| 1 | 292.2 g. | 100.0g. | 4.0 g. | 60.0g. | 60.0 g. | 80.0g. | 1403.8 g. |
| 2 | 292.2 g. | 100.0g. | | 60.0g. | 60.0 g. | 80.0g. | 1407.8 g. |
| 3 | 146.1 g. | 50.0g. | 2.0 g. | 30.0g. | 60.0 g. | 40.0g. | 671.9 g. |
| 4 | 29.22 g. | 10.0g. | 0.4 g. | 6.0g. | 12.0 g. | 8.0g. | 67.19 g. |
| 5 | 68.05 g. | 25.0g. | 1.0 g. | 15.0g. | 20.0 g. | 30.0g. | 340.95 g. |

Each of these compositions produced a suitable coating emulsion. The coating adhered to the polytetrafluoroethylene surface after drying and was an essentially continuous coating on the polytetrafluoroethylene tape. The polyphosphate content of the floss of Example 1 was 0.29 percent by weight and the fluoride content 104 ppm. The .flosses of Examples 2 through 5 exhibited good coatings and had an acceptable uptake of fluoride and the anti-calculus component of polyphosphate and Gantrez S-97.

Examples 6–8

These examples illustrate the coating of an expanded polytetrafluoroethylene tape having the dimensions of Examples 1–5 with flavorants. The tape is unwound from a spool and passed through a coating bath which contains the coating solution. The coated polytetrafluoroethylene tape is then dried and wound onto a spool. The coating solution for each of the examples is set out in Table II.

TABLE II

| Example | Polyvinyl Alcohol | Polyethylene Glycol | Flavorant* | Sodium Saccharin | Distilled Water |
|---|---|---|---|---|---|
| 6 | 25.0 g. | 10.0g. | 100.0g. | 2.5 g. | 362.5 g. |
| 7 | 42.0 g. | 15.0g. | 62.5g. | 3.75 g. | 376.75 g. |
| 8 | 20.0 g. | 4.0g. | 40.0g. | 1.0 g. | 135.0 g. |

*Mint Flavorant

Each of the examples yielded as essentially continuous coating on the polytetrafluoroethylene tape. There was also an acceptable degree of mint flavorant take-up and solvolysis during use.

Examples 9–10

Examples 9 and 10 set forth the coating of a polytetrafluoroethylene expanded tape floss having the characteristics of that of Examples 1–5 with a wax which contains a flavorant. The wax is a microcrystalline wax Wico W-455. The wax is melted by heating to 180° F. The flavorant was vigorously mixed into the molten wax so that it was dispersed in the wax. The polytetrafluoroethylene tape is run through the molten flavored wax bath and coated with the flavored wax. In Example 9, the flavorant content, of the wax 10 percent. In Example 10, the flavorant content of the wax was 20 percent. The flavored wax coated floss materials had an unacceptably low flavorant taste when used. Apparently, a sufficient amount of flavorant in the wax was not solvated so as to provide an acceptable taste.

Examples 11–12

In Examples 11 and 12, the polytetrafluoroethylene strand was first passed through a flavorant bath and then through a wax bath. In each example, the flavorant was mint. The wax was Witco W4-45 wax. In Example 11, the flavorant bath was maintained at room temperature and the wax bath at 200° F. The strand was passed through each bath at 3 ft. per second. In Example 12, the flavorant bath was maintained at room temperature and the wax bath at 160° F. The strand speed was the same as in Example 11. Each of these floss products had an unacceptably weak mint flavor taste during use. Apparently, not a sufficient amount of flavorant is solvated from the wax in order to produce an acceptable taste.

We claim:

1. An article for therapeutic oral use comprising a polytetrafluoroethylene surfaced article which has coated thereon an adjuvant composition containing a binder which can form a coating on polytetrafluoroethylene and which is at least partially water soluble and at least one adjuvant, which adjuvant is selected from the group consisting of flavorants, medicaments and mixtures thereof.

2. An article as in claim 1 wherein said binder comprises polyvinyl alcohol and polyethylene glycol.

3. An article as in claim 1 wherein said article is a toothpick and said adjuvant is selected from the group consisting of flavorants, medicants, and mixtures thereof.

4. An article as in claim 1 wherein said article is a tongue depressor and said adjuvant is selected from the group consisting of flavorants, medicants, and mixtures thereof.

5. An article as in claim 1 wherein said article is a dental floss and said adjuvant is selected from the group consisting of flavorants, medicants, and mixtures thereof 6. An article as in claim 5 wherein said article is a monofilament dental floss having a polytetrafluoroethylene surface and said medicant is selected from the group consisting of anti-calculus agents, fluorides, coagulants, antibiotics, and mixtures thereof.

7. An article as in claim 5 wherein said article is a multi-filament dental floss having a polytetrafluoroethylene surface and said medicant is selected from the group consisting of anti-calculus agents, fluorides, coagulants, antibiotics and mixtures thereof.

8. An article as in claim 2 wherein the adjuvant has been applied to said polytetrafluoroethylene surfaced article from an aqueous emulsion of from about 40 to 80 percent by weight water, about 5 to 20 percent by weight polyvinyl alcohol, about 10 to 40 percent by weight flavorant, about 0.25 to 1 percent by weight non-carbohydrate sweetener and about 1 to 4 percent by weight polyethylene glycol.

9. An article as in claim 1 wherein said adjuvant comprises a flavorant, a fluoride and as an anti-calculus agent, sodium tripolyphosphate and a polycarboxylate resin.

10. An article for cleaning teeth comprising a polytetrafluoroethylene surfaced monofilament having a thickness to width ratio of at least about 1 to 10 and coated with a composition comprised of at least one adjuvant and a coating agent which is at least partially water soluble to coat the adjuvant onto the polytetrafluoroethylene monofilament.

11. An article as in claim 10 wherein the thickness to width ratio of said polytetrafluoroethylene surfaced monofilament is from about 1 to 50 to about 1 to 500.

12. An article as in claim 10 wherein said polytetrafluoroethylene surfaced monofilament is a polytetrafluoroethylene monofilament.

13. An article as in claim 10 wherein said composition that is coated onto said polytetrafluoroethylene monofilament is comprised of an aqueous emulsion of polyvinyl alcohol, polyethylene glycol, and said adjuvant.

14. An article as in claim 13 wherein said aqueous emulsion is comprised of from about 40 to 80 percent by weight water, about 5 to 20 percent by weight polyvinyl alcohol, about 10 to 40 percent by weight adjuvant and about 1 to 4 percent by weight polyethylene glycol.

15. An article as in claim 13 wherein said adjuvant includes a medicant.

16. An article as in claim 13 wherein said adjuvant includes a flavorant.

17. An article as in claim 16 wherein said adjuvant includes a medicant selected from the group consisting of fluoride, coagulating agents, antibiotics, and an anti-calculus agent comprising sodium tripolyphosphate and a polycarboxylate.

18. An article for cleaning teeth comprising polytetrafluoroethylene surfaced multi-filaments coated with a composition comprised of an adjuvant and a coating binder which is at least partially water soluble, which adjuvant is selected from the group consisting of flavorants, medicaments and mixtures thereof.

19. An article for cleaning teeth as in claim 18 wherein said composition that is coated onto said polytetrafluoroethylene filaments is comprised of an aqueous emulsion of polyvinyl alcohol, polyethylene glycol, a non-carbohydrate sweetener and said adjuvant.

20. An article for cleaning teeth as in claim 19 wherein said aqueous emulsion is comprised of from about 40 to 80 percent by weight water, about 5 to 20 percent by weight polyvinyl alcohol, about 10 to 40 percent by weight adjuvant, about 0.25 to 1 percent by weight non-carbohydrate sweetener and about 1 to 4 percent by weight polyethylene glycol.

21. A method of making a flavored article for cleaning teeth comprising contacting at least one filament of polytetrafluoroethylene with an aqueous emulsion containing a flavorant and at least one medicament which is at least partially water soluble to bond the flavorant and medicament to said polytetrafluoroethylene filament, and drying the polytetrafluoroethylene filament.

22. A method of making a flavored article as in claim 21 wherein said filament is a monofilament having a thickness to width ratio of said polytetrafluoroethylene monofilament is from about 50 to 1 to about 500 to 1.

23. A method of making a flavored article as in claim 21 wherein said aqueous emulsion contains a non-carbohydrate sweetener.

24. A method of making a flavored article as in claim 21 wherein said aqueous emulsion contains polyvinyl alcohol, polyethylene glycol, a non-carbohydrate sweetener and said flavorant.

25. A method of making a flavored article as in claim 24 wherein said aqueous emulsion is comprised of form about 40 to 80 percent by weight water, about 5 to 20 percent by weight of polyvinyl alcohol, about 10 to 40 percent by weight flavorant, about 0.25 to 1 percent by weight non-carbohydrate sweetener and about 1 to 4 percent by weight polyethylene glycol.

26. A method of making a flavorant article as in claim 21 wherein the coated filaments are joined into a plurality of coated filaments.

* * * * *